(12) United States Patent
Kuhn et al.

(10) Patent No.: US 10,456,216 B2
(45) Date of Patent: Oct. 29, 2019

(54) DENTAL HAND INSTRUMENT AND HEAD HOUSING THEREFOR

(71) Applicant: KALTENBACH & VOIGT GMBH, Biberach (DE)

(72) Inventors: Bernhard Kuhn, Biberach (DE); Thomas Claßen, Herbertingen (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 223 days.

(21) Appl. No.: 14/840,832

(22) Filed: Aug. 31, 2015

(65) Prior Publication Data

US 2016/0074134 A1    Mar. 17, 2016

(30) Foreign Application Priority Data

Sep. 12, 2014 (EP) .................................. 14184579

(51) Int. Cl.
*A61C 1/12*        (2006.01)
*A61C 1/00*        (2006.01)
*A61C 1/14*        (2006.01)

(52) U.S. Cl.
CPC .............. *A61C 1/12* (2013.01); *A61C 1/0061* (2013.01); *A61C 1/0076* (2013.01); *A61C 1/141* (2013.01)

(58) Field of Classification Search
CPC ......... A61C 1/12; A61C 1/0076; A61C 1/141; A61C 1/0052; A61C 1/0061; A61C 17/16; A61C 17/024; A61C 17/36; A61C 17/0202; A61C 17/02
See application file for complete search history.

(56) References Cited

U.S. PATENT DOCUMENTS 5,697,784 A * 12/1997 Hafele .................. A61C 17/02
                                                        433/100
2008/0118890 A1* 5/2008 Knopp ................. A61C 1/0015
                                                        433/104

FOREIGN PATENT DOCUMENTS

EP    0 109 507 A1    5/1984
EP    1 025 809 A2    8/2000

* cited by examiner

*Primary Examiner* — Yogesh P Patel
*Assistant Examiner* — Stephen R Sparks
(74) *Attorney, Agent, or Firm* — Michael Best & Friedrich LLP

(57) ABSTRACT

In the case of a dental hand instrument having a grip sleeve and also a head housing arranged at the front end of the grip sleeve for receiving or holding a treatment instrument, the head housing has a substantially cylindrical hollow space which is connected by way of at least one connecting bore to a connection region pointing to the grip sleeve, wherein the connecting bore is coupled, at its end facing the grip sleeve, to a media line extending through the grip sleeve, and wherein the inner wall region of the head housing enclosing the hollow space has a recess into which the connecting bore opens.

10 Claims, 4 Drawing Sheets

DENTAL HAND INSTRUMENT AND HEAD HOUSING THEREFOR

CROSS-REFERENCE TO RELATED APPLICATIONS

The present invention claims priority to European Patent Application No. 14 184 579.2 filed on Sep. 12, 2014.

BACKGROUND OF THE INVENTION

The present invention relates to dental hand instruments and methods for using the same. In particular, the invention relates to mechanisms to receiving and holding a tool or treatment instrument in a dental hand instrument.

SUMMARY

Embodiments described in this disclosure provide a dental hand instrument with a grip sleeve and a head housing arranged at the front end of the grip sleeve for receiving or holding the treatment instrument. Furthermore, the present invention relates to a corresponding head housing for a dental hand instrument. The connection of the hand instrument and the head housing are configured to deliver a treatment, cleaning or cooling medium.

Dental hand instruments for carrying out treatments in the mouth area of a patient are usually designed in a manner to complement the processing of a tooth. For example, to deliver a medium that is used for cleaning or cooling purposes. The medium can be air, water, or an air-water mixture in the form of a spray.

A dental hand instrument of this kind usually has a grip sleeve with a head region, which is configured to receive or hold the treatment instrument, for example, a dental drill. The medium is delivered through this connection in a manner that directs the medium at the surface of the tooth to be processed by the dental drill. This is generally accomplished by arranging a spray insert in the lower region of the head housing. The spray insert is an annular component which is mounted in a cylindrical hollow space of the head housing and has media lines which open into corresponding delivery openings. The media lines of the spray insert are then coupled fluid-wise with corresponding media lines which extend through the hand instrument and the head housing.

In the case of the hand instruments usually used for dental treatment, the longitudinal axis of the head housing, thus determining, for example, the alignment of the drill, is arranged in such a manner that it is angled with respect to the longitudinal axis of the grip sleeve. Generally, two media lines are provided for compressed air and water. The media lines extend along the grip sleeve and open into two bores in the head housing. Sealing is effected in this case, for example, by way of elastic components resting against the lateral surfaces of the bores of the head housing or the media lines. The media made available by the two media lines are then generally forwarded by way of connecting bores that lead on, independently of each other, and connect the connection bores, into which the media lines extending through the grip sleeve open, to the inner geometry of the head housing. The head housing in this connection generally has a substantially cylindrical inner hollow space used for receiving the drive components and for holding the drill in which the spray insert is also arranged. The connecting bores that lead on and pass through the head housing thus open out in the inner region of the head housing in such a way that they merge into the mostly circumferential media channels of the spray insert inserted into the head housing.

One object of the invention is to make an improved solution available for forwarding the media. The object is achieved by providing a dental hand instrument having a grip sleeve and also a head housing arranged at the front end of the grip sleeve for receiving or holding a treatment instrument, wherein the head housing has a substantially cylindrical hollow space which is connected by way of at least one connecting bore to a connection region pointing to the grip sleeve, and wherein the connecting bore is coupled, at its end facing the grip sleeve, to a media line extending through the grip sleeve, and wherein the hollow space has a recess into which the connecting bore opens. The object is also achieved by means of a head housing for a dental hand instrument for receiving or holding a treatment instrument, wherein the head housing has a substantially cylindrical hollow space which is connected by way of at least one connecting bore to a connection region pointing to a grip sleeve of the hand instrument, and wherein the hollow space has a recess into which the connecting bore opens.

The solution provided in various embodiments of the invention is based on the idea of introducing into the region of the head housing, into which the connecting bores open, recesses, for example, in the form of milled slots, which extend the connecting bores in the region of transition to the media channels of the spray insert. These recesses, in accordance with the present invention, can then be configured as a function of the wall thickness of the head housing, for example, as sickle-shaped recesses or even as circumferential undercuts.

A dental hand instrument having a grip sleeve and also a head housing arranged at the front end of the grip sleeve for receiving or holding a treatment instrument is therefore proposed, wherein the head housing has a substantially cylindrical hollow space which is connected by way of at least one connecting bore to a connection region pointing to the grip sleeve, and wherein the connecting bore is coupled, at its end facing the grip sleeve, to a media line extending through the grip sleeve. The inner wall region enclosing the hollow space of the head housing has in this case at least one recess into which the connecting bore opens.

As is explained in greater detail in the following, the measure in accordance with the present invention results in it being possible for the overall height of the head housing to be reduced and in spite of all that for the hand instrument or in particular the head housing to be manufactured economically and with process reliability. A further advantage lies in the fact that the diameters of the connecting bores remain unaffected in the case of the solution in accordance with the present invention, that is, can be effected as they have been until now.

As a result of the large radii that develop when the recesses in accordance with the present invention are realized, the media are forwarded in a laminar manner into the circumferential undercuts, that is, into the media lines of the spray insert. This uniform distribution results in the spray mixture, which develops in the region of the exit point of the media, remaining constant and substantially unchanged over a large pressure range.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawing, wherein.

Figure 1:
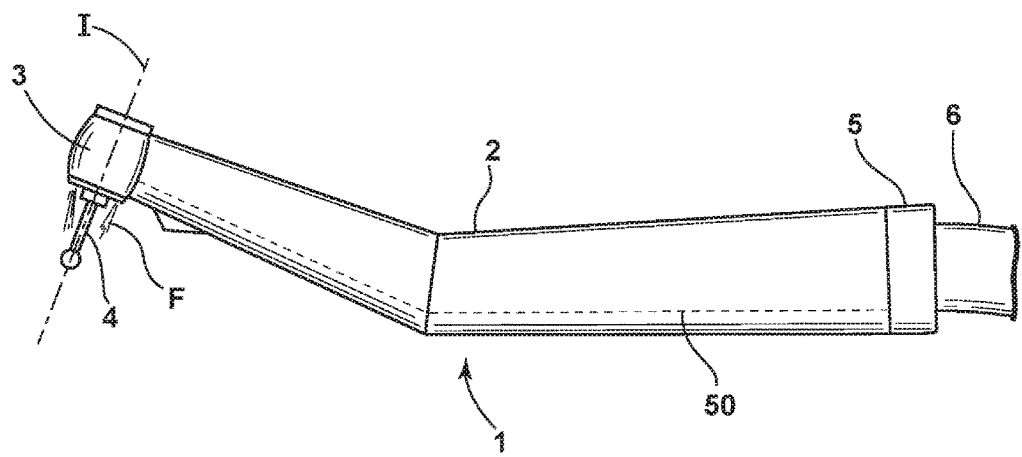
FIG. 1 is a perspective view of a dental hand instrument of the present invention.

Corresponding reference characters indicate corresponding parts throughout the several views. Although the drawings represent embodiments of the present invention, the drawings are not necessarily to scale and certain features may be exaggerated in order to better illustrate and explain the present invention. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION OF THE INVENTION

The embodiments hereinafter disclosed are not intended to be exhaustive or limit the invention to the precise forms disclosed in the following description. Rather the embodiments are chosen and described so that others skilled in the art may utilize its teachings.

FIG. 1 illustrates one example of a hand instrument 1 including a dental drill hand piece. It is to be pointed out that the solution in accordance with the present invention could also be applied in the case of other dental or surgical hand instruments.

The hand instrument 1 consists of an elongated grip sleeve 2. The elongated grip sleeve 2 is slightly angled for ergonomic reasons and as a result renders possible improved handling by a dentist. Located at the front end of the hand instrument 1 there is a head region 3. The head region 3, as compared to the adjacent region of the grip sleeve 2, is aligned so as to be approximately at right-angles. The head region 3 is designed in a manner to allow receipt of an attachable dental tool, for example, a dental drill 4. The head region 3 is allowed to receive the dental drill 4 by means of a collet chuck, which the dental drill 4 can be inserted and secured. The dental drill 4 or the collet chuck is then rotated by way of a drive system within the head region 3. For example, the drive system may be a turbine arranged in the head region 3. Additionally, for example, an electric motor arranged inside the elongated grip sleeve 2 in the hand piece or coupled to the hand piece as a separate unit may also drive the dental drill 4. At its rear end, the hand instrument 1 is rotatably connected by way of a coupling piece 5 to a supply hose 6 for the delivery of supply and treatment media, light, electrical energy, or combination thereof.

During the treatment of a tooth when the dental drill 4 is rotating, heat, which can be harmful to the tooth, develops on account of the friction. For this reason, it is desirable to cool, yet also clean the point of contact on the tooth that is to be processed during the treatment. To accomplish this, a medium in the form of a fluid is delivered at the underside of the head region 3 and directed onto the dental drill 4. Arranged on the underside of the head region 3 for this there is a spray insert 40 (shown in FIG. 4), which is connected to at least one media line 50 extending through the elongated grip sleeve 2 of the hand instrument 1. The spray insert 40 has at least one outlet by way of which a medium is directed onto the dental drill 4. The medium can be air, water, or an air-water mixture in the form of a spray. The medium can be directed onto the tooth that is to be processed for cleaning and cooling purposes.

Figure 5:
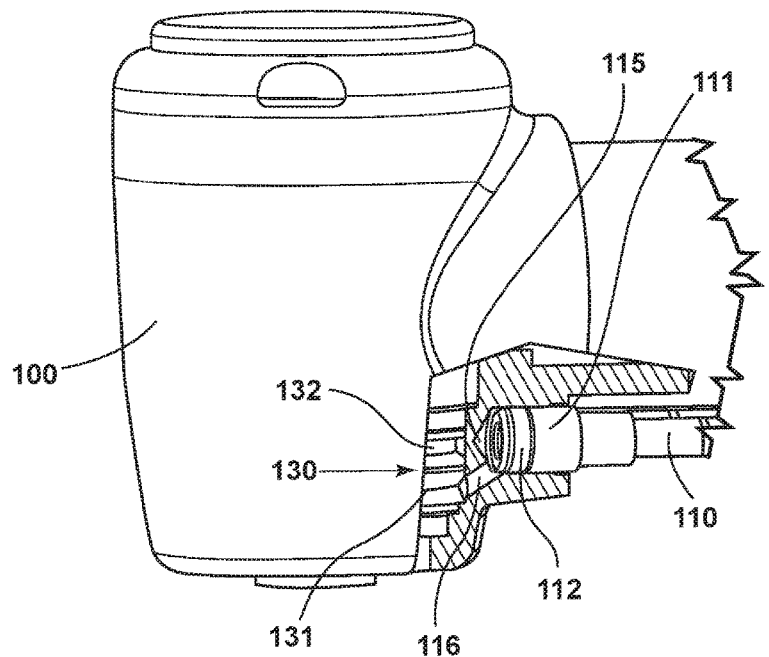
FIG. 5 is a perspective view of a configuration of a head housing of a dental hand instrument that is known from the prior art.
Figure 6:
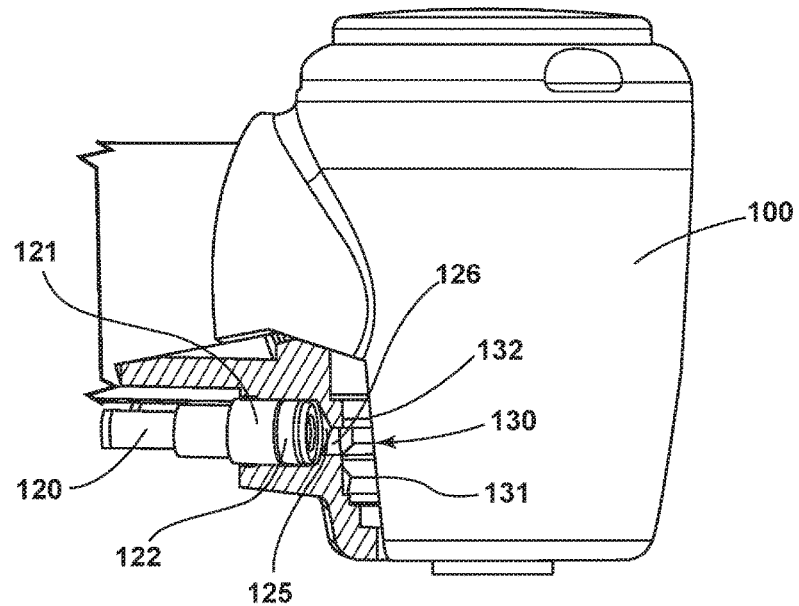
FIG. 6 is a perspective view of a configuration of a head housing of a dental hand instrument that is known from the prior art.
Figure 7:
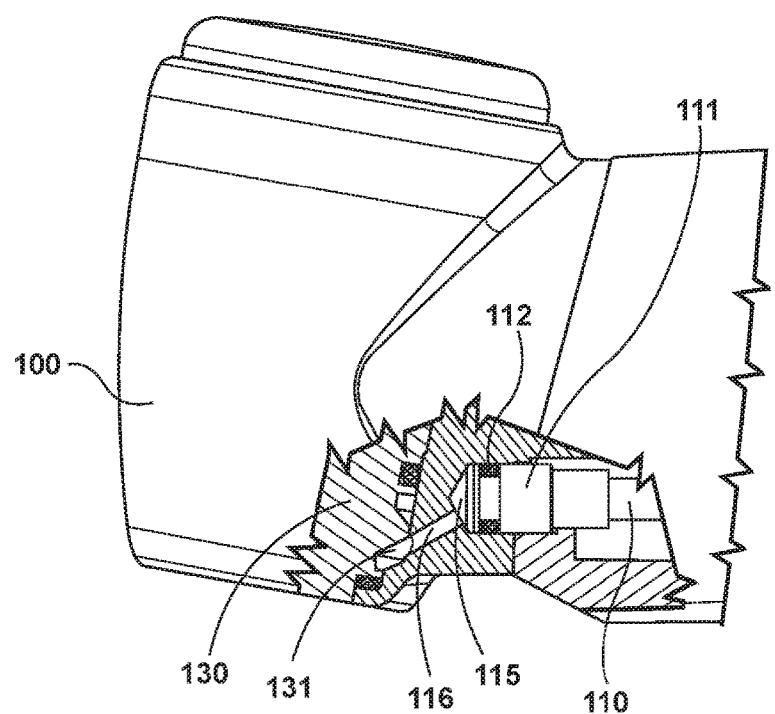
FIG. 7 is a perspective view of a configuration of a head housing of a dental hand instrument that is known from the prior art.

FIGS. 5-7 illustrate another example where it is possible to identify the end regions of the media lines 110 and 120 extending through the grip sleeve of the hand instrument 1 and opening, in each case, into the associated connection bore 115 and 125 respectively of the head housing 100. Furthermore, it is possible to identify that arranged at the front end of the media lines 110 and 120 there is a respective connection element 111 and 121 with a corresponding circumferential seal 112 and 122 in order to render possible a corresponding tight closure between the media lines 110 and 120 and connection region of the head housing 100.

Extending from the connection bores 115 and 125 are corresponding connecting bores 116 and 126 respectively. Connecting bores 116 and 126 open into the inner cylindrical receiving region of the head housing 100. Furthermore, a spray insert 130 is arranged in this inner cylindrical receiving region and has two circumferential annular grooves or incisions 131 and 132 forming circumferential media channels which are coupled to the transverse connecting bores 116 and 126. In other words, the transverse connecting bores 116 and 126 are in each case realized in such a way that they open into one of the two corresponding circumferential annular grooves 131 and 132. The circumferential annular grooves 131 and 132 are sealed by means of corresponding sealing elements 112 and 122. The circumferential annular grooves 131 and 132 then open into delivery openings by way of which the media are delivered either singly or as an air-water mixture, that is, as a spray. For this, the delivery openings are arranged on the underside of the spray insert 130 so as to be distributed around the dental drill 4 or the tool.

In the example of FIGS. 5 to 7, the two circumferential annular grooves 131 and 132 of the spray insert 130 forming the circumferential media channels are arranged in different planes. The transverse connecting bores 116 and 126, leading to at least one of the circumferential grooves 131 and 132, must therefore automatically be constructed so as to be inclined in comparison with the inner surface of the inner hollow space of the head housing 100. In this case, this applies to the transverse connecting bore 116 which, in accordance with the representations, leads to the lower circumferential annular groove 131.

The consequence of the angular position of the transverse connecting bore 116 is that at the exit point of the connecting bore 116 there is an elliptical opening which is automatically higher in the axial direction of the head housing 100 than the connecting bore 116 diameter itself. The width of the corresponding circumferential annular grove 131 must be adapted in a corresponding manner to the height of this elliptical exit opening of the connecting bores 116 and 126.

Such an adaptation requires a higher level of outlay in structural terms during the production of the head region 100.

It is to be taken into consideration in this connection that an optimum media supply can only be guaranteed when the cross-sections of the connecting bores 116 and 126 are adapted not only to the different prevailing pressure conditions of the media, but also to the structural design of the functionally relevant component periphery. Any diminution in the cross-sections for the connecting bores 116 and 126 is accordingly not possible. The circumferential grooves 131 and 132 of the spray insert 130 are clearly separated from each other spatially by a circumferential web or by a corresponding elastic sealing element 112 in order to ensure a uniform delivery of media. However, this configuration results in a greater overall height for the head region 3 of a dental hand instrument 1.

Referring back to FIG. 1, the media lines 50 extending through the grip sleeve thus lead to the head housing 9 and are guided on in the head housing 9 through connecting bores which lead to a substantially cylindrical hollow space in which inter alia the spray insert with the circumferential channels is arranged, as shown in FIGS. 5 to 7.

Figure 2:
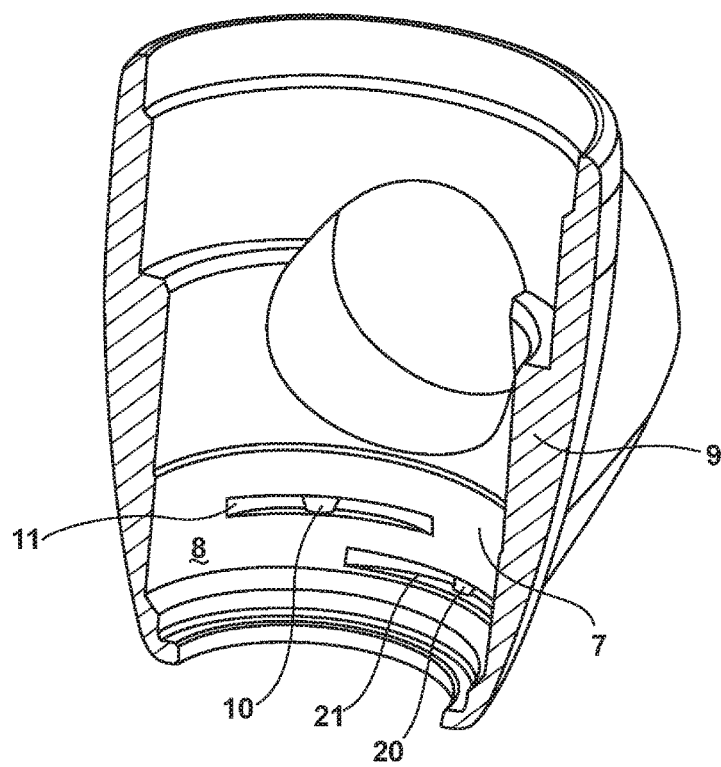
FIG. 2 is a cross-sectional view of an inner wall region of a head housing configured in accordance with the present invention for the dental hand instrument shown in FIG. 1.
Figure 3:
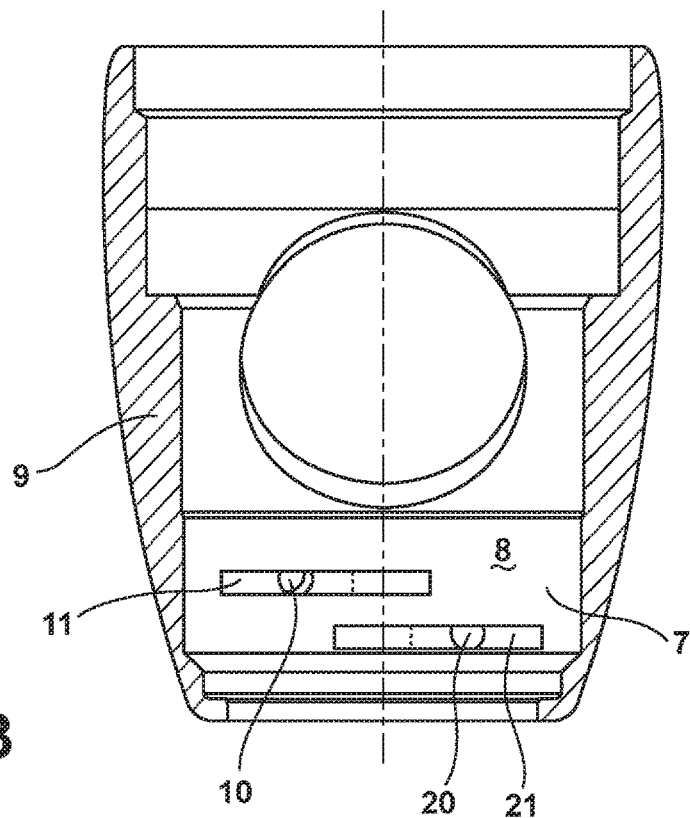
FIG. 3 is a cross-sectional view of an inner wall region of a head housing configured in accordance with the present invention for the dental hand instrument shown in FIG. 1.
Figure 4:
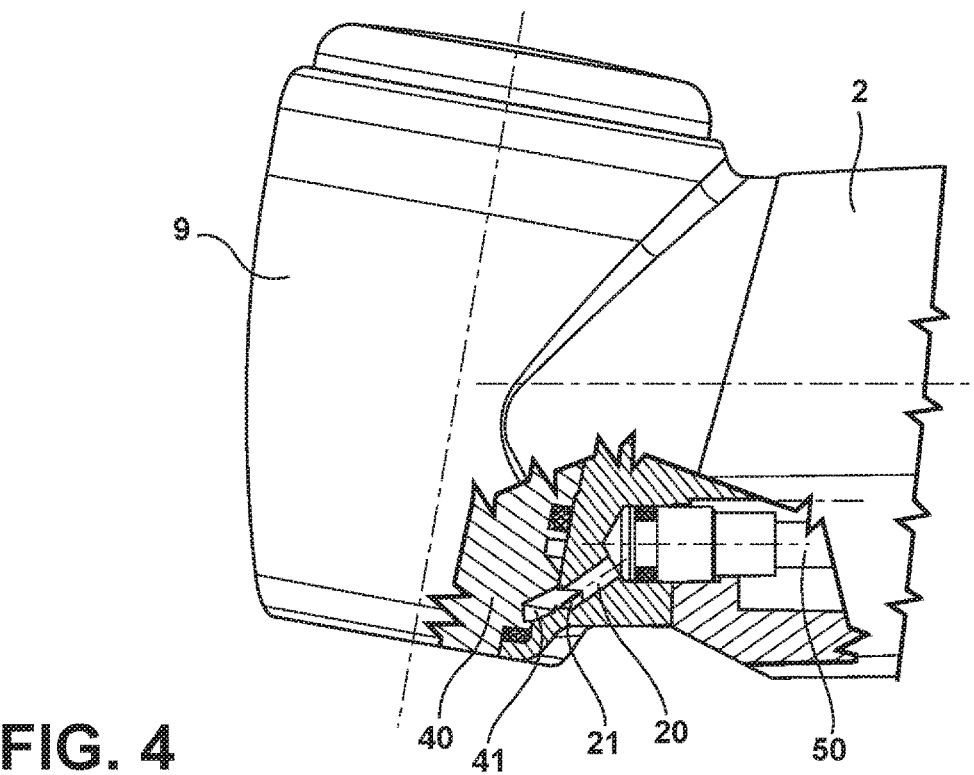
FIG. 4 is a perspective view of an inner wall region of a head housing configured in accordance with the present invention for the dental hand instrument shown in FIG. 1.

Referring now to FIGS. 2 to 4, the modification of the prior art configuration, in accordance with the present invention, is illustrated. The connecting bores 10 and 20 connect the connection region of the head housing 9 to the inner wall region 8 of the hollow space 7. At least one of the connecting bores 10 and 20 extends in an inclined manner with respect to the plane aligned perpendicularly to the longitudinal axis I (shown in FIG. 1). Furthermore, the connecting bores 10 and 20 do not open directly into the hollow space 7. Instead, the connecting bores 10 and 20 are extended by recesses 11 and 21 respectively.

The recesses 11 and 21 extend in a plane perpendicularly to the longitudinal axis I of the head housing 3 and in relation to the inner wall region 8 over a significantly greater extent than would be the case with the connecting bores 10 and 20 opening directly into the inner wall region 8. In the exemplary embodiment shown, as a result, when viewed in cross-section, a substantially sickle-shaped form results for the recesses 11 and 21. It would, however, also be possible in the same way for the recesses 11 and 21 to extend over the whole extent of the inner wall region 8 forming annular undercuts, in which case even a partially annular form would be possible.

The recesses 11 and 21 are arranged in such a way that the recesses 11 and 21 communicate with the corresponding circumferential undercuts 41 of the spray insert 40 (shown in FIG. 4). Thus, viewed in the axial direction, the recesses 11 and 21 are arranged at the same height as the circumferential undercuts 41 of the spray insert 40. Additionally, the recesses 11 and 21 preferably have an identical height. For example, the recesses 11 and 21 can be introduced into the head housing 3 with the aid of a correspondingly constructed T-slot miller. However, other methods for realizing the recesses 11 and 21 would also be possible, for example, eroding or broaching.

Because the recesses 11 and 21 extend or open the connecting bores 10 and 20, the overall height for the head housing 3 can be reduced. The transition to the media channels of the spray insert 40 is namely now defined by the recesses 11 and 21 and no longer by the connecting bores 10 and 20, aligned in an inclined manner. The recesses 11 and 21 can thus have a lower height in comparison with the connecting bores 10 and 20. This ultimately means that a corresponding reduction in height can also be effected in the case of the spray insert 40. Accordingly, the head housing 3 of the hand instrument 1 can be more compact overall.

Additionally, the transition of the media is even optimized. Since on account of the resultant larger region of transition to the spray insert 40, a more uniform and thus less pressure-sensitive distribution of the media at the transition points is attained. This in turn means that all the delivery openings for the media in the spray insert 40 can be supplied more uniformly and in a better way. Accordingly, the functionality overall is optimized. This improved transition results even when the associated connecting bores 10 and 20 do not extend in an inclined manner, but instead perpendicularly to the longitudinal axis I, and thus, to the surface of the inner hollow space 7. Consequently, in each case it is advantageous to provide the recesses 11 and 21 in accordance with the invention at both connecting bores 10 and 20.

Ultimately, the properties of a head housing 9 for a dental hand instrument 1 can thus be significantly improved with a measure that can be carried out comparatively simply. In particular, the overall height can be reduced, with in spite of all that the forwarding of the media even being improved. It is to be stressed in this connection in particular that these advantages are achieved without the connecting bores 10 and 20 having to be reduced further in terms of the cross-sections of the connecting bores 10 and 20.

What is claimed is:

1. A dental hand instrument, comprising:
   a grip sleeve having a front end;
   a head housing arranged at the front end of the grip sleeve, the head housing including a substantially cylindrical hollow space and an inner wall region enclosing the substantially hollow space, the head housing configured to receive or hold a treatment instrument;
   a spray insert arranged in the substantially cylindrical hollow space having two circumferential annular incisions;
   a connecting bore located in the head housing having a first end facing the grip sleeve,
      wherein the substantially cylindrical hollow space is connected by way of the connecting bore to a connection region pointing to the grip sleeve, and
      wherein the first end of the connecting bore is coupled to a media line extending through the grip sleeve; and
   a sickle-shaped recess located within the inner wall region of the head housing and into which the connecting bore opens.

2. A dental hand instrument of claim 1, wherein the connecting bore is aligned so as to be inclined with respect to a plane running perpendicularly to a longitudinal axis of the substantially cylindrical hollow space.

3. A dental hand instrument of claim 1, further comprising an insert piece arranged in the substantially cylindrical hollow space of the head housing, wherein the insert piece has a media channel communicating with the sickle-shaped recess.

4. A dental hand instrument of claim 3, wherein a height of the sickle-shaped recess corresponds to a height of the media channel.

5. A dental hand instrument of claim 1, wherein the head housing has a plurality of connecting bores, wherein each of the plurality of connecting bores opens into the sickle-shaped recess formed on the inner wall region of the head housing.

6. A head housing for a dental hand instrument for receiving or holding a treatment instrument, the head housing comprising:

a substantially cylindrical interior hollow space connected by way of at least one connecting bore to a connection region, the connecting bore and the connecting region located through the head housing grip sleeve of the hand instrument, a spray insert arranged in the substantially cylindrical hollow space having two circumferential annular incisions, and an inner wall region enclosing the substantially cylindrical hollow space and comprising a sickle-shaped recess into which the at least one connecting bore opens.

7. The head housing of claim 6, wherein the at least one connecting bore is aligned so as to be inclined with respect to a plane running perpendicularly to a longitudinal axis of the substantially cylindrical hollow space.

8. The head housing as claimed in claim 6, further comprising an insert piece arranged in the substantially cylindrical hollow space of the head housing, wherein the insert piece has a media channel communicating with the sickle-shaped recess.

9. The head housing as claimed in claim 7, wherein a height of the sickle-shaped recess corresponds to a height of the media channel.

10. The head housing of claim 6, wherein the head housing has a plurality of connecting bores, wherein each of the plurality of connecting bores opens into the sickle-shaped recess formed on the inner wall region.

\* \* \* \* \*